(12) United States Patent
Miyawaki et al.

(10) Patent No.: US 7,247,449 B2
(45) Date of Patent: Jul. 24, 2007

(54) FLUORESCENT PROTEIN

(75) Inventors: Atsushi Miyawaki, Wako (JP); Satoshi Karasawa, Tokyo (JP); Toshio Araki, Asaka (JP)

(73) Assignees: RIKEN, Saitama (JP); Medical & Biological Laboratories Co., Ltd., Aichi (JP)

( * ) Notice: Subject to any disclaimer, the term of this patent is extended or adjusted under 35 U.S.C. 154(b) by 190 days.

(21) Appl. No.: 10/492,081

(22) PCT Filed: Oct. 10, 2002

(86) PCT No.: PCT/JP02/10529

§ 371 (c)(1),
(2), (4) Date: Oct. 25, 2004

(87) PCT Pub. No.: WO03/033693

PCT Pub. Date: Apr. 24, 2003

(65) Prior Publication Data

US 2005/0106661 A1 May 19, 2005

(30) Foreign Application Priority Data

Oct. 11, 2001 (JP) .............................. 2003-313780

(51) Int. Cl.
C12P 21/06 (2006.01)
C07K 14/00 (2006.01)

(52) U.S. Cl. ................ 435/69.1; 435/320.1; 435/252.2; 536/23.1; 530/350

(58) Field of Classification Search ................ 530/350; 435/69.1, 320.1, 252.2; 536/23.1
See application file for complete search history.

(56) References Cited

U.S. PATENT DOCUMENTS

| 2003/0017538 A1 | 1/2003 | Miyawaki et al. |
| 2006/0154296 A1 | 7/2006 | Miyawaki et al. |
| 2006/0160990 A1 | 7/2006 | Miyawaki et al. |
| 2006/0240472 A1 | 10/2006 | Miyawaki et al. |

FOREIGN PATENT DOCUMENTS

| JP | 10-234382 | 9/1998 |
| WO | 00/28025 | 5/2000 |
| WO | 00/34526 | 6/2000 |
| WO | 03/054191 | 7/2003 |
| WO | 03/070952 | 8/2003 |
| WO | 2003/104460 | 12/2003 |
| WO | 2003/104461 | 12/2003 |
| WO | 2004/018671 | 4/2004 |
| WO | 2004/111235 | 12/2004 |
| WO | 2004/111236 | 12/2004 |
| WO | 2005/054464 | 6/2005 |

OTHER PUBLICATIONS

R.Y. Tsien, Ann. Rev. Biochem., vol. 67, pp. 509-544, 1998.
English Language abstract of JP 10-234382.
Geoffrey S. Baird et al., "Biochemistry, Mutagenesis, and Oligomerization of DsRed, a Red Fluorescent Protein From Coral", PNAS, vol. 97, No. 22, pp. 11984-11989 (2000).
U.S. Appl. No. 11/390,215 (Miyawaki et al.), filed Mar. 28, 2006 and entitled "A Method for Analysis of Protein Interaction using Fluorescent Protein".
U.S. Appl. No. 10/525,365 (Miyawaki et al.), filed Aug. 22, 2003 and entitled "Fluorescent protein and Chromoprotein".
U.S. Appl. No. 10/581,551 (Miyawaki et al.), filed Dec. 3, 2004 and entitled "Fluorescent Proteins".
U.S. Appl. No. 10/561,041 (Miyawaki et al.), filed Jun. 16, 2004 and entitled "Fluorescent Protein and Pigment Protein".
U.S. Appl. No. 10/561,040 (Miyawaki et al.), filed Jun. 16, 2004 and entitled "Fluorescent Protein".
U.S. Appl. No. 10/516,314 (Miyawaki et al.), filed Jun. 10, 2003 and entitled "Pigment Protein".
U.S. Appl. No. 10/516,317 (Miyawaki et al.), filed Jun. 10, 2003 and entitled "Pigment Protein".

*Primary Examiner*—Karen Cochrane Carlson
(74) *Attorney, Agent, or Firm*—Greenblum & Bernstein, P.L.C.

(57) ABSTRACT

An object of the present invention is to provide a novel fluorescent protein derived from organisms other than *Aequorea victoria*. According to the present invention, there is provided a fluorescent protein derived from *Galaxea fascicularis*, which has the following properties:
(1) the molecular weight is approximately 27,000;
(2) a tetramer is formed in an equilibration state;
(3) the excitation maximum wavelength is 492 nm, and the fluorescence maximum wavelength is 505 nm;
(4) the molar absorption coefficient is 74,100;
(5) the quantum yield is 0.625; and
(6) the pH sensitivity of the fluorescent property is low in the range between pH 5 and pH 12.

16 Claims, 11 Drawing Sheets

SEQUENCE LISTING

```
<160> NUMBER OF SEQ ID NOS: 12

<210> SEQ ID NO 1
<211> LENGTH: 225
<212> TYPE: PRT
<213> ORGANISM: Galaxea fascicularis

<400> SEQUENCE: 1

Met Ser Val Ile Lys Pro Glu Met Lys Ile Lys Leu Cys Met Arg Gly
1               5                   10                  15

Thr Val Asn Gly His Asn Phe Val Ile Glu Gly Glu Gly Lys Gly Asn
```

-continued

```
                    20                  25                  30
Pro Tyr Glu Gly Thr Gln Ile Leu Asp Leu Asn Val Thr Glu Gly Ala
     35                  40                  45

Pro Leu Pro Phe Ala Tyr Asp Ile Leu Thr Thr Val Phe Gln Tyr Gly
 50                  55                  60

Asn Arg Ala Phe Thr Lys Tyr Pro Ala Asp Ile Gln Asp Tyr Phe Lys
 65                  70                  75                  80

Gln Thr Phe Pro Glu Gly Tyr His Trp Glu Arg Ser Met Thr Tyr Glu
                 85                  90                  95

Asp Gln Gly Ile Cys Thr Ala Thr Ser Asn Ile Ser Met Arg Gly Asp
                100                 105                 110

Cys Phe Phe Tyr Asp Ile Arg Phe Asp Gly Val Asn Phe Pro Pro Asn
                115                 120                 125

Gly Pro Val Met Gln Lys Lys Thr Leu Lys Trp Glu Pro Ser Thr Glu
            130                 135                 140

Lys Met Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Lys Thr Thr
                    165                 170                 175

Tyr Lys Ala Lys Lys Asp Val Arg Leu Pro Asp Tyr His Phe Val Asp
                180                 185                 190

His Arg Ile Glu Ile Leu Lys His Asp Lys Asp Tyr Asn Lys Val Lys
            195                 200                 205

Leu Tyr Glu Asn Ala Val Ala Arg Tyr Ser Met Leu Pro Ser Gln Ala
    210                 215                 220

Lys
225
```

<210> SEQ ID NO 2
<211> LENGTH: 678
<212> TYPE: DNA
<213> ORGANISM: Galaxea fascicularis

<400> SEQUENCE: 2

```
atgagtgtga ttaaaccaga gatgaaaatc aagctgtgta tgagaggcac tgtaaacggg      60
cataatttcg tgattgaagg agaaggaaaa ggaaatcctt acgagggaac gcagattta     120 gacctgaacg tcactgaagg cgcacctctg cctttcgctt acgatatctt gacaacagtg    180
ttccagtacg gcaacagggc attcaccaag tacccagcag atattcagga ctatttcaag    240
cagacttttc ctgaggggta tcactgggaa agaagcatga cttatgaaga ccagggcatt    300
tgcaccgcca caagcaacat aagcatgcgt ggcgactgtt ttttctatga cattcgtttt    360
gatggtgtga actttcctcc caatggtccg gttatgcaga agaagactct taaatgggag    420
ccatccactg agaaaatgta cgtacgtgat ggagtgctga agggtgatgt aacatggct     480 ctgttgcttg aaggaggtgg ccattatcga tgtgatttca aaactactta caaagcaaag    540
aaggatgtcc gtttgccaga ctatcacttt gtggaccacc gcattgagat tttgaagcat    600
gacaaagatt acaacaaggt caagctctat gagaatgccg ttgctcgcta ttctatgctg    660
ccgagtcagg ccaagtaa                                                  678
```

<210> SEQ ID NO 3
<211> LENGTH: 21
<212> TYPE: DNA
<213> ORGANISM: Artificial Sequence
<220> FEATURE:

<223> OTHER INFORMATION: Synthetic DNA

<400> SEQUENCE: 3
gaaggrtgyg tcaayggrca y                                              21

<210> SEQ ID NO 4
<211> LENGTH: 23
<212> TYPE: DNA
<213> ORGANISM: Artificial Sequence
<220> FEATURE:
<223> OTHER INFORMATION: Synthetic DNA

<400> SEQUENCE: 4
acvggdccat ydgvaagaaa rtt                                            23

<210> SEQ ID NO 5
<211> LENGTH: 36
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (24)..(35)
<223> OTHER INFORMATION: n is inosine
<220> FEATURE:
<221> NAME/KEY: misc_feature
<222> LOCATION: (24)..(25)
<223> OTHER INFORMATION: n is inosine
<220> FEATURE:
<221> NAME/KEY: misc_feature
<222> LOCATION: (29)..(30)
<223> OTHER INFORMATION: n is inosine
<220> FEATURE:
<221> NAME/KEY: misc_feature
<222> LOCATION: (34)..(35)
<223> OTHER INFORMATION: n is inosine

<400> SEQUENCE: 5
ggccacgcgt cgactagtac gggnngggnn gggnng                              36

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

<400> SEQUENCE: 6
aaaagtctgc ttgaaatagt                                                20

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA

<400> SEQUENCE: 7
ggccacgcgt cgactagtac                                                20

<210> SEQ ID NO 8
<211> LENGTH: 19
<212> TYPE: DNA
<213> ORGANISM: Artificial Sequence
<220> FEATURE:
<223> OTHER INFORMATION: Synthetic DNA

<400> SEQUENCE: 8

```
tgtcaagata tcgtaagcg                                                    19

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
actatttcaa gcagactttt                                                   20

<210> SEQ ID NO 10
<211> LENGTH: 42
<212> TYPE: DNA
<213> ORGANISM: Artificial Sequence
<220> FEATURE:
<223> OTHER INFORMATION: Synthetic DNA

<400> SEQUENCE: 10
cgggatccac catggtgagt gtgattaaac cagagatgaa aa                           42

<210> SEQ ID NO 11
<211> LENGTH: 35
<212> TYPE: DNA
<213> ORGANISM: Artificial Sequence
<220> FEATURE:
<223> OTHER INFORMATION: Synthetic DNA

<400> SEQUENCE: 11
tccgctcgag cttggcctga ctcggcagca tagaa                                  35

<210> SEQ ID NO 12
<211> LENGTH: 225
<212> TYPE: PRT
<213> ORGANISM: Galaxea fascicularis

<400> SEQUENCE: 12

Met Ser Val Ile Lys Pro Glu Met Lys Ile Lys Leu Cys Met Arg Gly
1               5                   10                  15

Thr Val Asn Gly His Asn Phe Val Ile Glu Gly Glu Gly Lys Gly Asn
            20                  25                  30

Pro Tyr Glu Gly Thr Gln Ile Leu Asp Leu Asn Val Thr Glu Gly Ala
        35                  40                  45

Pro Leu Pro Phe Ala Tyr Asp Ile Leu Thr Thr Val Phe Gln Tyr Gly
    50                  55                  60

Asn Arg Ala Phe Thr Lys Tyr Pro Ala Asp Ile Gln Asp Tyr Phe Lys
65                  70                  75                  80

Gln Thr Phe Pro Glu Gly Tyr His Trp Glu Arg Ser Met Thr Tyr Glu
                85                  90                  95

Asp Gln Gly Ile Cys Thr Ala Thr Ser Asn Ile Ser Met Arg Gly Asp
            100                 105                 110

Cys Phe Phe Tyr Asp Ile Arg Phe Asp Gly Val Asn Phe Pro Pro Asn
        115                 120                 125

Gly Pro Val Met Gln Lys Lys Thr Leu Lys Trp Glu Pro Ser Thr Glu
    130                 135                 140

Lys Met Tyr Val Arg Asp Gly Val Leu Lys Gly Asp Val Asn Met Ala
145                 150                 155                 160

Leu Leu Leu Glu Gly Gly His Tyr Arg Cys Asp Phe Lys Thr Thr
                165                 170                 175
```

```
Tyr Lys Ala Lys Lys Asp Val Arg Leu Pro Asp Tyr His Phe Val Asp
            180                 185                 190

His Arg Ile Glu Ile Leu Lys His Asp Lys Asp Tyr Asn Lys Val Lys
        195                 200                 205

Leu Tyr Glu Asn Ala Val Ala Arg Tyr Ser Met Leu Pro Ser Gln Ala
    210                 215                 220

Lys
225
```

FLUORESCENT PROTEIN

TECHNICAL FIELD

The present invention relates to a novel fluorescent protein having improved properties. More specifically, the present invention relates to a novel fluorescent protein derived from *Galaxea fascicularis*, and the use thereof.

BACKGROUND ART

Green fluorescent protein (GFP) derived from *Aequorea victoria*, a jellyfish, has many purposes in biological systems. Recently, various GFP mutants have been produced based on the random mutagenesis and semi-rational mutagenesis, wherein a color is changed, a folding property is improved, luminance is enhanced, or pH sensitivity is modified. Fluorescent proteins such as GFP are fused with other proteins by gene recombinant technique, and monitoring of the expression and transportation of the fusion proteins is carried out.

One of the most commonly used types of GFP mutant is Yellow fluorescent protein (YFP). Among Aequorea-derived GFP mutants, YFP exhibits the fluorescence with the longest wavelength. The values ε and Φ of the majority of YEPs are 60,000 to 100,000 $M^{-1}$ $cm^{-1}$ and 0.6 to 0.8, respectively (Tsien, R. Y. (1998). Ann. Rev. Biochem. 67, 509-544). These values are comparable to those of the general fluorescent group (fluorescein, rhodamine, etc.). Accordingly, improvement of the absolute luminance of YFP is nearly approaching its limit.

DISCLOSURE OF THE INVENTION

An object of the present invention is to provide a novel fluorescent protein derived from organisms other than *Aequorea victoria*. Another object of the present invention is to provide a novel fluorescent protein having improved fluorescent properties as compared with the fluorescent protein derived from *Aequorea Victoria*.

In order to achieve the above objects, the present inventors have conducted intensive studies. The present inventors have designed suitable primers based on the amino acid sequences of known fluorescent proteins. They have succeeded in amplifying a fluorescent protein from the cDNA library of *Galaxea fascicularis* exhibiting fluorescence, using the above primers, and cloning such proteins. Further, the present inventors have examined the fluorescent properties of the obtained fluorescent protein derived from *Galaxea fascicularis*, and as a result, they have found that this fluorescent protein has desired fluorescent properties. The present invention has been completed based on these findings.

Thus, the present invention provides a fluorescent protein derived from *Galaxea fascicularis*, which has the following properties:

(1) the molecular weight is approximately 27,000;
(2) a tetramer is formed in an equilibration state;
(3) the excitation maximum wavelength is 492 nm, and the fluorescence maximum wavelength is 505 nm;
(4) the molar absorption coefficient is 74,100;
(5) the quantum yield is 0.625; and
(6) the pH sensitivity of the fluorescent property is low in the range between pH 5 and pH 12.

In another aspect of the present invention, there is provided a fluorescent protein having either one of the following amino acid sequences:

(a) an amino acid sequence shown in SEQ ID NO: 1; or (b) an amino acid sequence comprising a deletion, substitution and/or addition of one or several amino acids with respect to the amino acid sequence shown in SEQ ID NO: 1, and having fluorescent properties.

In another aspect of the present invention, there is provided a fluorescent protein having an amino acid sequence wherein Gln at position 76 is substituted with Arg, Asn at position 106 is substituted with Asp, Ile at position 118 is substituted with Thr, Asp at position 150 is substituted with Gly, and Val at position 157 is substituted with Asp, with respect to the amino acid sequence shown in SEQ ID NO: 1.

In another aspect of the present invention, there is provided a fluorescent protein wherein Val at position 123 is substituted with Thr, Tyr at position 188 is substituted with Ala, and Phe at position 190 is substituted with Lys, with respect to the amino acid sequence shown in SEQ ID NO: 1.

In another aspect of the present invention, there is provided DNA which encodes the above-described fluorescent protein of the present invention.

In another aspect of the present invention, there is provided DNA of either one of the following:

(a) NA which encodes the amino acid sequence shown in SEQ ID NO: 1; or (b) DNA which encodes an amino acid sequence comprising a deletion, substitution and/or addition of one or several amino acids with respect to the amino acid sequence shown in SEQ ID NO: 1, and having fluorescent properties.

In another aspect of the present invention, there is provided DNA having either one of the following nucleotide sequences:

(a) a nucleotide sequence shown in SEQ ID NO: 2; or (b) a nucleotide sequence comprising a deletion, substitution and/or addition of one or several nucleotides with respect of the nucleotide sequence shown in SEQ ID NO: 2, and encoding a protein having fluorescent properties.

In another aspect of the present invention, there is provided a recombinant vector having the above-described DNA of the present invention.

In another aspect of the present invention, there is provided a transformant having the above-described DNA or recombinant vector of the present invention.

In another aspect of the present invention, there is provided a fusion fluorescent protein consisting of the above-described fluorescent protein of the present invention and another protein. Preferably, said another protein is one that localizes in the cell, and more preferably, said another protein is one specific to an intracellular organella.

In another aspect of the present invention, there is provided a method for analyzing the localization or dynamics of a protein in cells, characterized in that the above-described fusion protein of the present invention is allowed to be expressed in cells.

In another aspect of the present invention, there is provided a fluorescent reagent kit which comprises the above-described fluorescent protein, DNA, recombinant vector, transformant or fusion protein according to the present invention.

BEST MODE FOR CARRYING OUT THE INVENTION

Figure 1:
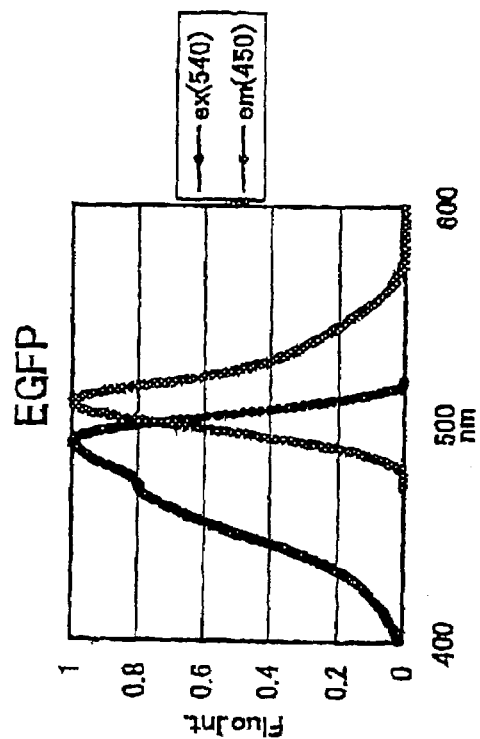
FIG. 1 shows the results of analysis of the fluorescent properties of the fluorescent protein (Azami-Green) derived from coral of the present invention and EGFP.
Figure 1:
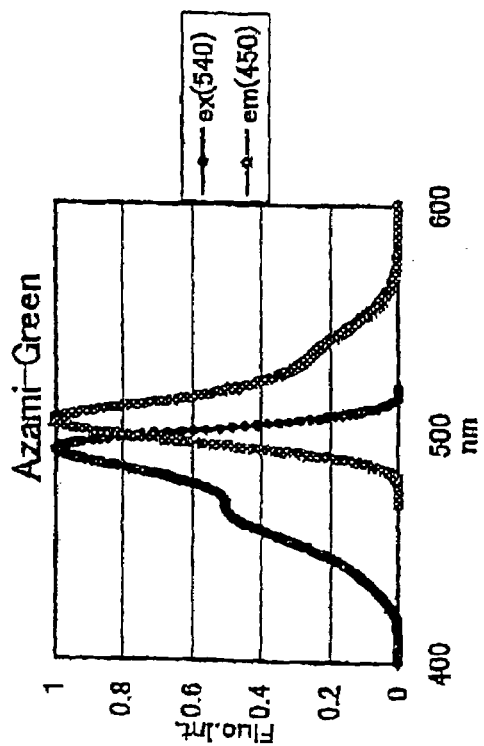

The embodiments of the present invention will be described in detail below.

(1) Fluorescent Protein of the Present Invention

The fluorescent protein of the present invention is characterized in that it is derived from *Galaxea fascicularis* and has the following properties:
(1) the molecular weight is approximately 27,000;
(2) a tetramer is formed in an equilibration state;
(3) the excitation-maximum wavelength is 492 nm, and the fluorescence maximum wavelength is 505 nm;
(4) the molar absorption coefficient is 74,100;
(5) the quantum yield is 0.625; and
(6) the pH sensitivity of the fluorescent properties is low in the range between pH 5 and pH 12.

*Galaxea fascicularis* is one type of coral. Its outer shape as a coral colony is hemispherical, but it may adopt a platy or columnar shape. Each coral polyp adopts an angular oblong shape, and a large number of sharply pointed diaphragms project therefrom.

In Examples of the present specification described later, the fluorescent protein of the present invention having the above properties was isolated by using *Galaxea fascicularis* as a starting material. However, in some cases, the fluorescent protein of the present invention can be obtained also from coral which emits fluorescence other than *Galaxea fascicularis*. Such fluorescent proteins are also included in the scope of the present invention.

The fluorescent protein of the present invention has a molecular weight of approximately 27,000, and it forms a tetramer in an equilibration state. It also forms a 8-mer, although in a small amount. The molecular weight of the tetramer is approximately 116 kDa, and the molecular weight of the 8-mer is approximately 204 kDa. The term "equilibration state" is used to mean a state in which, for example, the fluorescent protein of the present invention is equilibrated with 50 mM HEPES (pH 7.5) and 150 mM KCl. Moreover, the formation of multimers can be measured by measuring light scattering. When light is applied to fine particles, the majority of the particles are scattered with the same light wavelength. This phenomenon is known as Rayleigh scattering. The intensity of this scattered light becomes a function of the number of the fine particles and the size thereof. Using this principle, molecular weight is derived from the value that is obtained by a light scattering detector. More specifically, the fluorescent protein of the present invention is equilibrated with 50 mM HEPES (pH 7.5) and 150 mM KCl, and then, first, the equilibrated solution containing the fluorescent protein of the present invention is divided by gel filtration in terms of molecular weight. Subsequently, the scattered light and the concentration of the sample are measured by a multi-angle light scattering detector and an RI detector, respectively, so that the molecular weight is obtained as a value.

As described in Examples mentioned later, the fluorescent protein of the present invention has an excitation maximum wavelength of 492 nm and a fluorescence maximum wavelength of 505 nm. It has a molar absorption coefficient of 74,100 and a quantum yield of 0.625. In contrast, EGFP (Clontech) has a molar absorption coefficient of 44,800 and a quantum yield of 0.600. Molar absorption coefficient represents the amount of photons absorbed per mole of fluorescent molecules. Quantum yield is a value showing what amount of the absorbed photons can be emitted as a fluorescence. Accordingly, the increased values of the molar absorption coefficient and quantum yield indicate that fluorescence is strong. Therefore, the fluorescent protein of the present invention, whose molar absorption coefficient and quantum yield are greater than those of EGFP, emits a fluorescence which is stronger than that of EGFP. With regard to excitation and fluorescence maximum wavelengths, there are no significant differences between EGFP and the fluorescent protein of the present invention. However, since the excitation and fluorescence spectrums of the fluorescent protein of the present invention are sharper than those of EGFP, it can be said that the fluorescent protein of the present invention is advantageous in terms of multicolor imaging performed in combination with other fluorescent molecules, etc.

The fluorescent protein of the present invention is characterized in that the pH sensitivity of the fluorescent properties is low in the range between pH 5 and pH 12. This is to say, a fluctuation in the peak value of fluorescence intensity is small in the range between pH 5 and pH 12, and thus, high fluorescence intensity can be maintained in this pH range. In the case of the conventionally used EGFP, since fluorescence intensity decreases at pH 7 or less, limitation is put on its use In vivo. However, the fluorescent protein of the present invention is free from such limitation.

The examples of the fluorescent protein of the present invention include a fluorescent protein having either one of the following amino acid sequences:
(a) an amino acid sequence shown in SEQ ID NO: 1; or
(b) an amino acid sequence comprising a deletion; substitution and/or addition of one or several amino acids with respect to the amino acid sequence shown in SEQ ID NO: 1, and having fluorescent properties.

The scope of "one or several" in the phrase "an amino acid sequence comprising a deletion, substitution and/or addition of one or several amino acids" is not particularly limited in the present specification. For example, it means 1 to 20, preferably 1 to 10, more preferably 1 to 7, further preferably 1 to 5, and particularly preferably 1 to 3.

The term "fluorescent properties" in (b) above means any given fluorescent properties. The fluorescent properties may be equivalent to those of the fluorescent protein having the amino acid sequence shown in SEQ ID NO: 1, such as fluorescence intensity, excitation wavelength, fluorescence wavelength or pH sensitivity, or may be different from them.

A fluorescent protein having an amino acid sequence wherein Gln at position 76 is substituted with Arg, Asn at position 106 is substituted with Asp, Ile at position 118 is substituted with Thr, Asp at position 150 is substituted with Gly, and Val at position 157 is substituted with Asp, with respect to the amino acid sequence shown in SEQ ID NO: 1, is one example of the fluorescent protein having the above mutation. This fluorescent protein has an excitation peak at 380 nm and at 484 nm, and its fluorescence spectrum shows its peak at 501 nm with any type of excitation. The major excitation peak is at 380 nm, and the Stokes shift is 120 nm, which is an extremely large value. The minor excitation peak at 484 nm increases from pH 6 to pH 10, but the excitation peak at 380 nm does not change. Accordingly, by measuring the ratio of fluorescence values obtained by excitation lights at 380 nm and at 484 nm, it becomes possible to measure pH in vitro or in cells. Among the conventional *Aequorea victoria*-derived GFPs, there is a modified protein (pHluorin), the pH of which can be measured by a fluctuation in two excitation peaks. Differing from the case of AG-pH, however, one peak does not take a constant value in this protein. Accordingly, the fluorescence in the aforementioned fluorescent protein can be measured by exciting the peak at 380 nm without being influenced by pH.

A fluorescent protein having an amino acid sequence wherein Val at position 123 is substituted with Thr, Tyr at position 188 is substituted with Ala, and Phe at position 190 is substituted with Lys, with respect to the amino acid sequence shown in SEQ ID NO: 1, is another example of the fluorescent protein having the above mutation. This protein exists in the form of a monomer. The molecular weight of this protein was determined by the light scattering method to be 34 kDa. This monomeric fluorescent protein has a fluorescence maximum wavelength of 505 nm and an excitation maximum wavelength of 492 nm, which are the same values of those of the fluorescent protein having the amino acid sequence shown in SEQ ID NO: 1.

The method of obtaining the fluorescent protein of the present invention is not particularly limited. The protein may be either a protein synthesized by chemosynthesis, or recombinant protein produced by a gene recombination technique.

Where a recombinant protein is produced, it is necessary to obtain DNA encoding the protein. Appropriate primers are designed from information regarding the amino acid sequence shown in SEQ ID NO: 1 of the sequence listing of the present specification and the nucleotide sequence shown in SEQ ID NO: 2 thereof. Using these primers, PCR is carried out by using cDNA clones of the above-described various types of known fluorescent proteins as a template, so that DNA encoding the fluorescent protein of the present invention can be obtained. Where a partial fragment of DNA encoding the fluorescent protein of the present invention are obtained by the above-described PCR, the produced DNA fragments are ligated to one another by a gene recombination technique, so that DNA encoding the desired fluorescent protein can be obtained. The fluorescent protein of the present invention can be produced by introducing this DNA into an appropriate expression system. Expression in an expression system will be described later in the present specification.

(2) DNA of the Present Invention

According to the present invention, a gene encoding the fluorescent protein of the present invention is provided.

Specific examples of DNA encoding the fluorescent protein of the present invention may include either one of the following DNAs:
(a) DNA which encodes the amino acid sequence shown in SEQ ID NO: 1; and
(b) DNA which encodes an amino acid sequence comprising a deletion, substitution and/or addition of one or several amino acids with respect to the amino acid sequence shown in SEQ ID NO: 1, and having fluorescent properties.

Specific examples of DNA encoding the fluorescent protein of the present invention may also include those having either one of the following nucleotide sequences:
(a) a nucleotide sequence shown in SEQ ID NO: 2; or
(b) a nucleotide sequence comprising a deletion, substitution and/or addition of one or several nucleotides with respect of the nucleotide sequence shown in SEQ ID NO: 2, and encoding a protein having fluorescent properties.

The DNA of the present invention can be synthesized by, for example, the phosphoamidite method, or it can also be produced by polymerase chain reaction (PCR) using specific primers. The DNA of the present invention or a fragment thereof is produced by the method described above in the specification.

A method of introducing a desired mutation into a certain nucleic acid sequence is known to a person skilled in the art. For example, known techniques such as a site-directed mutagenesis, PCR using degenerated oligonucleotides, or the exposure of cells containing nucleic acid to mutagens or radioactive rays, are appropriately used, so as to construct DNA having a mutation. Such known techniques are described in, for example, Molecular Cloning: A Laboratory, Manual, $2^{nd}$ Ed., Cold, Spring Harbor Laboratory, Cold Spring Harbor, N.Y., 1989; and Current Protocols in Molecular Biology, Supplements 1 to 38, John Wiley & Sons (1987-1997).

(3) Recombinant Vector of the Present Invention

The DNA of the present invention can be inserted into a suitable vector and used. The type of a vector used in the present invention is not particularly limited. For example, it may be either a vector that can autonomously replicate (e.g., a plasmid, etc.), or vector that is incorporated into the genomes of host cells when it is introduced into the host cells and is then replicated together with the chromosome into which it is incorporated.

The vector used in the present invention is preferably an expression vector. In an expression vector, elements necessary for transcription (e.g., a promoter, etc.) are functionally ligated to the DNA of the present invention. The promoter is a DNA sequence which shows a transcriptional activity in host cells, and it is appropriately selected depending on the type of host cells.

Examples of a promoter which can operate in bacterial cells may include a *Bacillus stearothermophilus* maltogenic amylase gene promoter, a *Bacillus licheniformis* alpha-amylase gene promoter, a *Bacillus amyloliquefaciens* BAN amylase gene promoter, a *Bacillus subtilis* alkaline protease gene promoter, a *Bacillus pumilus* xylosidase gene promoter, $P_R$ and $P_L$ promoters of phage rhamda, and lac, trp and tac promoters of *Escherichia coli*.

Examples of a promoter which can operate in mammalian cells may include an SV40 promoter, an MT-1 (metallothionein gene) promoter, and an adenovirus-2 major late promoter. Examples of a promoter which can operate in insect cells may include a polyhedrin promoter, a P10 promoter, an *Autographa californica* polyhedrosis basic protein promoter, a baculovirus immediate-early gene 1 promoter, and a baculovirus 39K delayed-early gene promoter. Examples of a promoter which can be operate in yeast host cells may include promoters derived from yeast glycolytic genes, an alcohol dehydrogenase gene promoter, a TPI1 promoter, and an ADH2-4c promoter.

Examples of a promoter which can operate in filamentous cells may include an ADH3 promoter and a tpiA promoter.

In addition, an appropriate terminator such as a human growth hormone terminator, or a TPI1 terminator or ADH3 terminator for fungal cells, may be functionally bound to the DNA of the present invention, as necessary. The recombinant vector of the present invention may further have elements such as a polyadenylation signal (e.g., one derived from SV40 or the adenovirus 5E1b region), a transcription enhancer sequence (e.g., an SV40 enhancer), or a translation enhancer sequence (e.g., one encoding the adenovirus VA RNA).

The recombinant vector of the present invention may further comprise a DNA sequence which enables the replication of the recombinant vector in host cells. SV40 replication origin is an example of such a sequence (when the host cells are mammalian cells).

The recombinant vector of the present invention may further comprise a selective marker. Examples of such a selective marker may include genes, complements of which are absent from host cells, such as a dihydrofolate reductase (DHFR) gene or a *Shizosaccharomyces pombe* TPI gene, and drug resistant genes such as ampicillin, kanamycin, tetracycline, chloramphenicol, neomycin or hygromycin-resistant genes.

A method for ligating the DNA of the present invention, a promoter and, as desired, a terminator and/or a secretory signal sequence to one another and inserting these items into a suitable vector is known to a person skilled in the art.

(4) Transformant of the Present Invention

A transformant can be produced by introducing the DNA or recombinant vector of the present invention into a suitable host.

Any cell can be used as a host cell into which the DNA or recombinant vector of the present invention is introduced, as long as the DNA construct of the present invention can be expressed therein. Examples of such a cell may include bacteria, yeasts, fungal cells, and higher eukaryotic cells.

Examples of bacteria may include Gram-positive bacteria such as *Bacillus* or *Streptomyces*, and Gram-negative bacteria such as *Escherichia coli*. These bacteria may be transformed by the protoplast method or other known methods, using competent cells.

Examples of mammalian cells may include HEK 293 cells, HeLa cells, COS cells, BHK cells, CHL cells, and CHO cells. A method of transforming mammalian cells and expressing the introduced DNA sequence in the cells is also known. Examples of such a method may include the electroporation, the calcium phosphate method, and the lipofection method.

Examples of yeast cells may include those belonging to *Saccharomyces* or *Shizosaccharomyces*. Examples of such cells may include *Saccharomyces cerevisiae* and *Saccharomyces kluyveri*. Examples of a method of introducing a recombinant vector into yeast host cells may include the electroporation, the spheroplast method, and the lithium acetate method.

Examples of other fungal cells may include those belonging to *Filamentous fungi* such as *Aspergillus, Neurospora, Fusarium* or *Trichoderma*. Where *Filamentous fungi* are used as host cells, transformation can be carried out by incorporating DNA constructs into host chromosomes, so as to obtain recombinant host cells. Incorporation of DNA constructs into the host chromosomes is carried out by known methods, and such known methods may include homologous recombination and heterologous recombination.

Where insect cells are used as host cells, both a vector into which a recombinant gene is introduced and a baculovirus are co-introduced into insect cells, and a recombinant virus is obtained in the culture supernatant of the insect cells. Thereafter, insect cells are infected with the, recombinant virus, so as to allow the cells to express proteins (described in, for example, Baculovirus Expression Vectors, A Laboratory Manual; and Current Protocols in Molecular Biology, Bio/Technology, 6, 47 (1988)).

The *Autographa californica* nuclear polyhedrosis virus, which is a virus infecting to insects belonging to *Barathra brassicae*, can be used as baculovirus.

Examples of insect cells used herein may include Sf9 and Sf21, which are *Spodoptera frugiperda* ovarian cells [Baculovirus Expression Vectors, A Laboratory Manual, W. H. Freeman & Company, New York, (1992)], and HiFive (manufactured by Invitrogen), which are *Trichoplusia ni* ovarian cells.

Examples of the method of co-introducing both a vector into which a recombinant gene has been introduced and the above baculovirus into insect cells to prepare a recombinant virus may include the calcium phosphate method and the lipofection method.

The above transformant is cultured in an appropriate nutritive medium under conditions enabling the introduced DNA construct to be expressed. In order to isolate and purify the fusion fluorescent protein of the present invention from the culture product of the transformant, common methods of isolating and purifying proteins may be used.

For example, where the protein of the present invention is expressed in a state dissolved in cells; after completion of the culture, cells are recovered by centrifugal separation, and the recovered cells are suspended in a water type buffer. Thereafter, the cells are disintegrated using an ultrasonic disintegrator or the like, so as to obtain a cell-free extract. A supernatant is obtained by centrifuging the cell-free extract, and then, a purified sample can be obtained from the supernatant by applying, singly or in combination, the following ordinary protein isolation and purification methods: the solvent extraction, the salting-out method using ammonium sulfate or the like, the desalting method, the precipitation method using an organic solvent, the anion exchange chromatography using resins such as diethylaminoethyl (DEAE) sepharose, the cation exchange chromatography using resins such as S-Sepharose FF (manufactured by Pharmacia), the hydrophobic chromatography using resins such as butyl sepharose or phenyl sepharose, the gel filtration method using a molecular sieve, the affinity chromatography, the chromatofocusing method, and the electrophoresis such as isoelectric focusing.

(5) Use of the Fluorescent Protein of the Present Invention and a Fusion Fluorescent Protein Comprising the Same The fluorescent protein of the present invention can be fused with another protein, so as to construct a fusion fluorescent protein.

A method of obtaining the fusion fluorescent protein of the present invention is not particularly limited. It may be either a protein synthesized by chemosynthesis, or recombinant protein produced by a gene recombination technique.

Where a recombinant protein is produced, it is necessary to obtain DNA encoding the protein. Appropriate primers are designed using the information regarding the amino acid sequence shown in SEQ ID NO: 1 of the sequence listing of the present specification and the nucleotide sequence shown in SEQ ID NO: 2 thereof. Using these primers, PCR is carried out using a DNA fragment containing the gene of the fluorescent protein of the present invention as a template, so as to produce DNA fragments necessary for construction of the DNA encoding the fluorescent protein of the present invention. Moreover, DNA fragments encoding a protein to be fused is also obtained in the same above manner.

Subsequently, the thus obtained DNA fragments are ligated to one another by a gene recombination technique, so that DNA encoding the desired fusion fluorescent protein can be obtained. This DNA is then introduced into an appropriate expression system, so that the fusion fluorescent protein of the present invention can be produced.

The fluorescent protein of the present invention has an extremely high utility value as a marker. This is to say, the fluorescent protein of the present invention is purified as a fusion protein with an amino acid sequence to be tested, and the fusion protein is introduced into cells by methods such as the microinjection. By observing the distribution of the fusion protein over time, targeting activity of the amino acid sequence to be tested can be detected in the cells.

The type of another protein (an amino acid sequence to be tested) with which the fluorescent protein of the present invention is fused is not particularly limited. Preferred examples may include proteins localizing in cells, proteins specific for intracellular organelles, and targeting signals (e.g., a nuclear transport signal, a mitochondrial presequence, etc.). In addition, the fluorescent protein of the present invention can be expressed in cells and used, as well as being introduced into cells by the microinjection or the like. In this case, a vector into which the DNA encoding the fluorescent protein of the present invention is inserted in such a way that it can be expressed, is introduced into host cells.

Moreover, the fluorescent protein of the present invention can also be used as a reporter protein to determine promoter activity. This is to say, a vector is constructed such that DNA encoding the fluorescent protein of the present invention is located downstream of a promoter to be tested, and the vector is then introduced into host cells. By detecting the fluorescence of the fluorescent protein of the present invention which is emitted from the cells, the activity of the promoter to be tested can be determined. The type of a promoter to be tested is not particularly limited, as long as it operates in host cells.

A vector used to detect the targeting activity of the above amino acid sequence to be tested or to determine promoter activity is not particularly limited. Examples of a vector preferably used for animal cells may include pNEO (P. Southern, and P. Berg (1982) J. Mol. Appl. Genet. 1: 327), pCAGGS (H. Niwa, K. Yamamura, and 3. Miyazaki, Gene 108, 193-200 (1991)), pRc/CMV (manufactured by Invitrogen), and pCDM8 (manufactured by Invitrogen). Examples of a vector preferably used for yeasts may include pRS303, pRS304, pRS305, pRS306, pRS313, pRS314, pRS315, pRS316 (R. S. Sikorski and P. Hieter (1989) Genetics 122: 19-27), pRS423, pRS424, pRS425, pRS426 (T. W. Christianson, R. S. Sikorski, M. Dante, J. H. Shero, and P. Hieter (1992) Gene 110: 119-122).

In addition, the type of cells used herein is also not particularly limited. Various types of animal cells such as L cells, BalbC-3T3 cells, NIH3T3 cells, CHO (Chinese hamster ovary) cells, HeLa cells or NRK (normal rat kidney) cells, yeast cells such as *Saccharomyces cerevisiae*, *Escherichia coli* cells, or the like can be used. Vector can be introduced into host cells by common methods such as the calcium phosphate method or the electroporation.

The above obtained fusion fluorescent protein of the present invention wherein the fluorescent protein of the present invention is fused with another protein (referred to as a protein X) is allowed to be expressed in cells. By monitoring a fluorescence emitted, it becomes possible to analyze the localization or dynamics of the protein X in cells. That is, cells transformed or transfected with DNA encoding the fusion fluorescent protein of the present invention are observed with a fluorescence microscope, so that the localization and dynamics of the protein X in the cells can be visualized and thus analyzed.

For example, by using a protein specific for an intracellular organella as a protein X, the distribution and movement of a nucleus, a mitochondria, an endoplasmic reticulum, a Golgi body, a secretory vesicle, a peroxisome, etc., can be observed.

Moreover, for example, axis cylinders or dendrites of the nerve cells show an extremely complicated change in strikes in an individual who is under development. Accordingly, fluorescent labeling of these sites-enables a dynamic analysis.

The fluorescence of the fluorescent protein of the present invention can be detected with a viable cell. Such detection can be carried out using, for example, a fluorescence microscope (Axiophoto Filter Set 09 manufactured by Carl Zeiss) or an image analyzer (Digital Image Analyzer manufactured by ATTO).

The type of a microscope can be appropriately selected depending on purposes, Where frequent observation such as pursuit of a change over time is carried out, an ordinary incident-light fluorescence microscope is preferable. Where observation is carried out while resolution is emphasized, for example, in the case of searching localization in cells specifically, a confocal laser scanning microscope is preferable. In terms of maintenance of the physiological state of cells and prevention from contamination, an inverted microscope is preferable as a microscope system. When an erecting microscope with a high-powered lens is used, a water immersion lens can be used.

A filter set can be appropriately selected depending on the fluorescence wavelength of a fluorescent protein. In the case of the fluorescent protein of the present invention, a filter having an excitation light between approximately 470 and 490 nm and a fluorescence between approximately 500 and 560 nm can be preferably used.

When viable cells are observed over time using a fluorescence microscope, a high sensitive cooled CCD camera is used, since photography is carried out in a short time. In the case of the cooled CCD camera, CCD is cooled to decrease thermal noise, so that a weak fluorescence image can be clearly photographed by exposure in a short time.

(6) Kit of the Present Invention

The present invention provides a kit for analyzing the localization, of intracellular components and/or analyzing physiologically active substances, which is characterized in that it comprises at least one selected from the fluorescent protein, the fusion fluorescent protein, the DNA, the recombinant vector, or the transformant, which are described in the present specification. The kit of the present invention can be produced from commonly used materials that are known per se, by using common methods.

Reagents such as the fluorescent protein or the DNA are dissolved in an appropriate solvent, so that the reagents can be prepared in a form suitable for conservation. Water, ethanol, various types of buffer solution, etc, can be used as such a solvent.

The present invention will be further described in the following examples. However, the present invention is not limited by these examples.

EXAMPLES

Example 1

Isolation of a Novel Fluorescent Protein Gene (Azami-Green) From Coral (1) Extraction of Total RNA A fluorescent protein gene was isolated from coral which emits a fluorescence. *Galaxea fascicularis* was used as a material. *Galaxea fascicularis* was crushed with a hammer. 15 ml of "TRIxol" (GIBCO BRL) was added to 8 g of the crushed coral, and the mixture was stirred, followed by centrifugal separation at 1,500×g for 10 minutes. 3 ml of chloroform was added to the obtained supernatant, and the mixture was stirred for 15 seconds, followed by leaving at rest for 3 minutes. Thereafter, the mixture was centrifuged at 7,500×g for 15 minutes. 7.5 ml of isopropanol was added to the obtained supernatant, and the mixture was stirred for 15 seconds, followed by leaving at rest for 10 minutes. Thereafter, the mixture was centrifuged at 17,000×g for 10 minutes. The obtained supernatant was discarded. 6 ml of 70% ethanol was added to the residue, and the mixture was centrifuged at 17,000×g for 10 minutes. The obtained supernatant was discarded, and the precipitate was then dissolved in 200 μl of DEPC water. Total RNA dissolved in the DEPC water was diluted 100 times, and the O.D.260 and O.D.280 values were measured to determine RNA concentration. 300 μg of the total RNA was obtained.

(2) Synthesis of First Strand cDNA cDNA (33 μl) was synthesized from 3 μg of the total RNA using a kit for synthesizing first strand cDNA "Ready To Go" (Amersham Pharmacia).

(3) Degenerated PCR

PCR was carried out using 3 μl of the synthesized first strand cDNA (33 μl) as a template.

Primers were designed and produced such that regions similar to the amino acid sequences of known fluorescent proteins were picked up and such regions were converted into nucleotide sequences The sequences of the used primers are shown below:

(SEQ ID NO: 3)
5'-GAAGGRTGYGTCAAYGGRCAY-3' (primer 1);

and (SEQ ID NO: 4)
5'-ACVGGDCCATYDGVAAGAAARTT-3' (primer 2).

wherein R represents A or G, Y represents C or T, V represents A, C or G, and D represents A, G or T.

A PCR reaction solution having the following composition was used:

| Template (first strand cDNA) | 3 μl |
| x10 taq buffer | 5 μl |
| 2.5 mM dNTPs | 4 μl |
| 100 μM primer 1 | 1 μl |
| 100 μM primer 2 | 1 μl |
| Milli-Q | 35 μl |
| Taq polymerase (5 U/μl) | 1 μl |

The following PCR reaction conditions were applied:

94° C.×1 minute (PAD)

94° C.×30 seconds (Denaturation)

52° C.×30 seconds (Annealing)

72° C.×1 minute (Primer elongation)

A cycle consisting of the above 3 steps was repeated 30 times. The annealing temperature was decreased by 0.3° C. each cycle. This is to say, the temperature was 43° C. when 30 cycles were completed.

72° C.×7 minutes (Final elongation)

4° C. (Retention)

Using 1 μl of the amplified product obtained in the first PCR reaction as a template, PCR was carried out again under the same conditions. A 350 bp band of the expected size was cut out and purified by agarose gel electrophoresis.

(4) Subcloning and Sequencing

The purified DNA fragment was ligated to a pT7-blue vector (Novagen). *Escherichia coli* (TG1) was transformed therewith and then subjected to blue white selection. Plasmid DNA was purified from white colonies *Escherichia coli*, and the nucleotide sequence of the inserted DNA fragment was determined using a DNA sequencer. Thereafter, the obtained nucleotide sequence was compared with the nucleotide sequences of other fluorescent protein genes, so as to judge whether or not the nucleotide sequence of the DNA fragment was derived from a fluorescent protein. With regard to those that were judged to be a part of the fluorescent protein genes, the full-length gene was cloned by the 5'RACE method and the 3'-RACE method.

(5) 5'-RACE Method

In order to determine a nucleotide sequence on the 5'-side to the DNA fragment obtained by the Degenerated PCR, the 5'-RACE method was applied using 5'-RACE System for Rapid Amplification of cDNA Ends, Version 2.0 (GIBCO BRL). 3 μg of the total RNA prepared in (1) above was used as a template.

The following primers were used in the first amplification of dC-tailed cDNA:

(SEQ ID NO: 5)
5'-GGCCACGCGTCGACTAGTACGGGIIGGGIIGGGIIG-3';

and (SEQ ID NO: 6)
5'-AAAAGTCTGCTTGAAATAGT-3' wherein I represents inosine.

The following primers were used in the second amplification:

```
5'-GGCCACGCGTCGACTAGTAC-3';      (SEQ ID NO: 7)

and

5'-TGTCAAGATATCGTAAGCG-3'.       (SEQ ID NO: 8)
```

PCR reaction conditions were applied in accordance with protocols attached to the kit. The amplified 300 bp band was cut out and purified by agarose gel electrophoresis. The purified DNA fragment was ligated to a pT7-blue vector (Novagen). *Escherichia coli* (TG1) was transformed therewith and then subjected to blue white selection. Plasmid DNA was purified from white colonies *Escherichia coli*, and the nucleotide sequence of the inserted DNA fragment was determined using a DNA sequencer.

(6) 3'-RACE Method

A nucleotide sequence on the 3'-side to the DNA fragment obtained by the Degenerated PCR was obtained by PCR, using the primer prepared based on the information obtained by determination of the nucleotide sequence in (4) above and an oligo dT primer. 3 µl of the first strand cDNA prepared in (2) above was used as a template; The prepared primer was 5'-ACTATTTCAAGCAGACTTTT-3' (primer 3) (SEQ ID NO: 9).

A PCR reaction solution having the following composition was used:

| | |
|---|---|
| Template (first strand cDNA) | 3 µl |
| x10 taq buffer | 5 µl |
| 2.5 mM dNTPs | 4 µl |
| 20 µM primer 3 | 1 µl |
| 10 µM oligo dT primer | 1 µl |
| Milli-Q | 35 µl |
| Taq polymerase (5 U/µl) | 1 µl |

The following PCR reaction conditions were applied:
94° C.×1 minute (PAD)
94° C.×30 seconds (Denaturation)
55° C.×30 seconds (Annealing)
72° C.×1 minute (Primer elongation)
A cycle consisting of the above 3 steps was repeated 30 times.
72° C.×7 minutes (Final elongation)
4° C. (Retention)

The amplified 850 bp band was cut and purified by agarose gel electrophoresis. The purified DNA fragment was ligated to a pT7-blue vector (Novagen). *Escherichia coli* (TG1) was transformed therewith and then subjected to blue white selection. Plasmid DNA was purified from white colonies *Escherichia coli*, and the nucleotide sequence of the inserted DNA fragment was determined using a DNA sequencer.

(7) Expression of Protein in *Eseherichia coli*

From the obtained full-length nucleotide sequence, primers corresponding to the N-terminus and C-terminus of the protein were prepared. Thereafter, PCR was carried out using the first strand cDNA prepared in (2) above as template. The entire nucleotide sequence and the entire amino acid sequence are shown in SEQ ID NOS: 1, 2, and 12 of the sequence listing.

The used primers are as follows:

```
                                              (SEQ ID NO: 10)
5'-CGGGATCCACCATGGTGAGTGTGATTAAACCAGAGATGAAAA-3'
(primer 4);

and (SEQ ID NO: 11)
5'-TCCGCTCGAGCTTGGCCTGACTCGGCAGCATAGAA-3'
(primer 5).
```

A PCR reaction solution having the following composition was used:

| | |
|---|---|
| Template (first strand cDNA) | 3 µl |
| x10 pyrobest buffer | 5 µl |
| 2.5 mM dNTPs | 4 µl |
| 20 µM primer 4 | 1 µl |
| 20 µM primer 5 | 1 µl |
| Milli-Q | 35 µl |
| Pyrobest polymerase (5 U/µl) | 1 µl |

The following PCR reaction conditions were applied:
94° C.×1 minute (PAD)
94° C.×30 seconds (Denaturation)
55° C.×30 seconds (Annealing)
72° C.×1 minute (Primer elongation)
A cycle consisting of the above 3 steps was repeated 30 times.
72° C.×7 minutes (Final elongation)
4° C. (Retention)

The amplified 700 bp band was cut out and purified by agarose gel electrophoresis. The purified DNA fragment was subcloned into the NcoI and XhoI sites of a pET28 vector (Novagen), and it was allowed to be expressed in *Escherichia coli* (JM109-DE3). The expressed protein was constructed such that His-tag was attached to the C-terminus thereof, and thus, it was purified with Ni-Agarose gel (QIAGEN). Purification was carried out in accordance with the attached protocols. Subsequently, the properties of the purified protein were analyzed.

(8) Analysis of Fluorescent Properties

Using absolution of 20 µM fluorescent protein (molecular weight: 27026.52) and 50 mM HERES (pH 7.5), the absorption spectrum was measured. Thereafter, the molar absorption coefficient was calculated from the value of the peak (492 nm) of the spectrum. The fluorescent protein was diluted with the above buffer solution such that the absorption at 450 nm became 0.003. Its fluorescence spectrum by exciting at 450 nm and its excitation spectrum by a fluorescence at 540 nm were measured. Likewise, EGFP (Clontech) was diluted such that the absorption at 450 nm became 0.003, and its fluorescence spectrum was measured. Setting the quantum yield of EGFP to 0.6, the quantum yield of the cloned fluorescent protein was measured.

The results are shown in Table 1 and FIG. 1.

TABLE 1

Comparison between the fluorescent protein (Azami-Green) of the present invention derived from coral and EGFP

| | Azami-Green | EGFP |
|---|---|---|
| Excitation maximum | 492 nm | 490 nm |
| Fluorescence maximum | 505 nm | 509 nm |

TABLE 1-continued

Comparison between the fluorescent protein (Azami-Green) of the present invention derived from coral and EGFP

|  | Azami-Green | EGFP |
| --- | --- | --- |
| Molar absorption coefficient | 74100 | 48850 |
| Quantum yield | 0.625 | 0.600 |
| Formation of multimer | Tetramer | Monomer |
| pH sensitivity | None | pKa = 6.0 |
| Number of amino acids | 225 | 238 |
| Expression in animal cells | Possible | Possible |

(9) Measurement of pH Sensitivity

Figure 2:
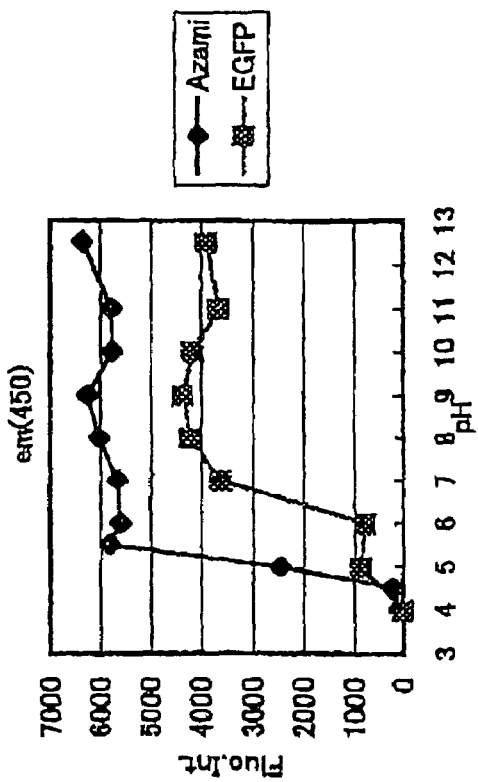
FIG. 2 shows pH sensitivity of the fluorescence intensity of the fluorescent protein (Azami-Green) derived from coral of the present invention and EGFP.
Figure 2:
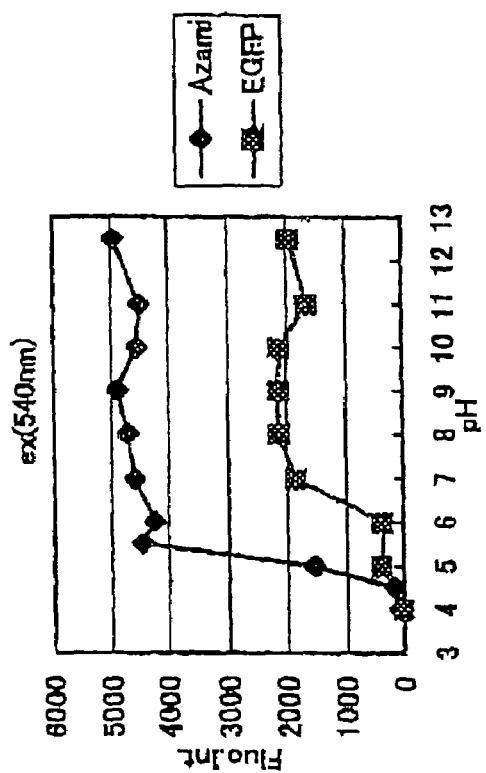

The fluorescent protein was diluted with 50 mM HEPES (pH 7.5) such that the absorption at 450 nm became 0.003. Its fluorescence spectrum by exciting at 450 nm and its excitation spectrum by a fluorescence at 540 nm were measured. Likewise, EGFP (Clontech) was diluted such that the absorption at 450 nm became 0.003 at pH 7.5, and its fluorescence spectrum was measured. This was used as a control. The following buffer solutions were used for each pH.

pH 4, 4.5, and 5: Acetate buffer
pH 5.5, 6.5, and 11: Phosphate buffer
pH 6: MES buffer
pH 7: MOPS buffer
pH 8: HEPES buffer
pH 9 and 10: Glycine buffer
pH 12.5: Hydroxychloride buffer Measurement results are shown in FIG. 2.

(10) Measurement of Formation of Multimer

The fluorescent protein was equilibrated with 50 mM HEPES (pH 7.5) and 150 mM KCl. Measurement of the formation of multimers by light scattering was conducted by Shoko Co., Ltd. As a result of the measurement, it was confirmed that this fluorescent protein formed tetramers (116 K) and only a small amount of 8-mers (204 K).

Figure 3:
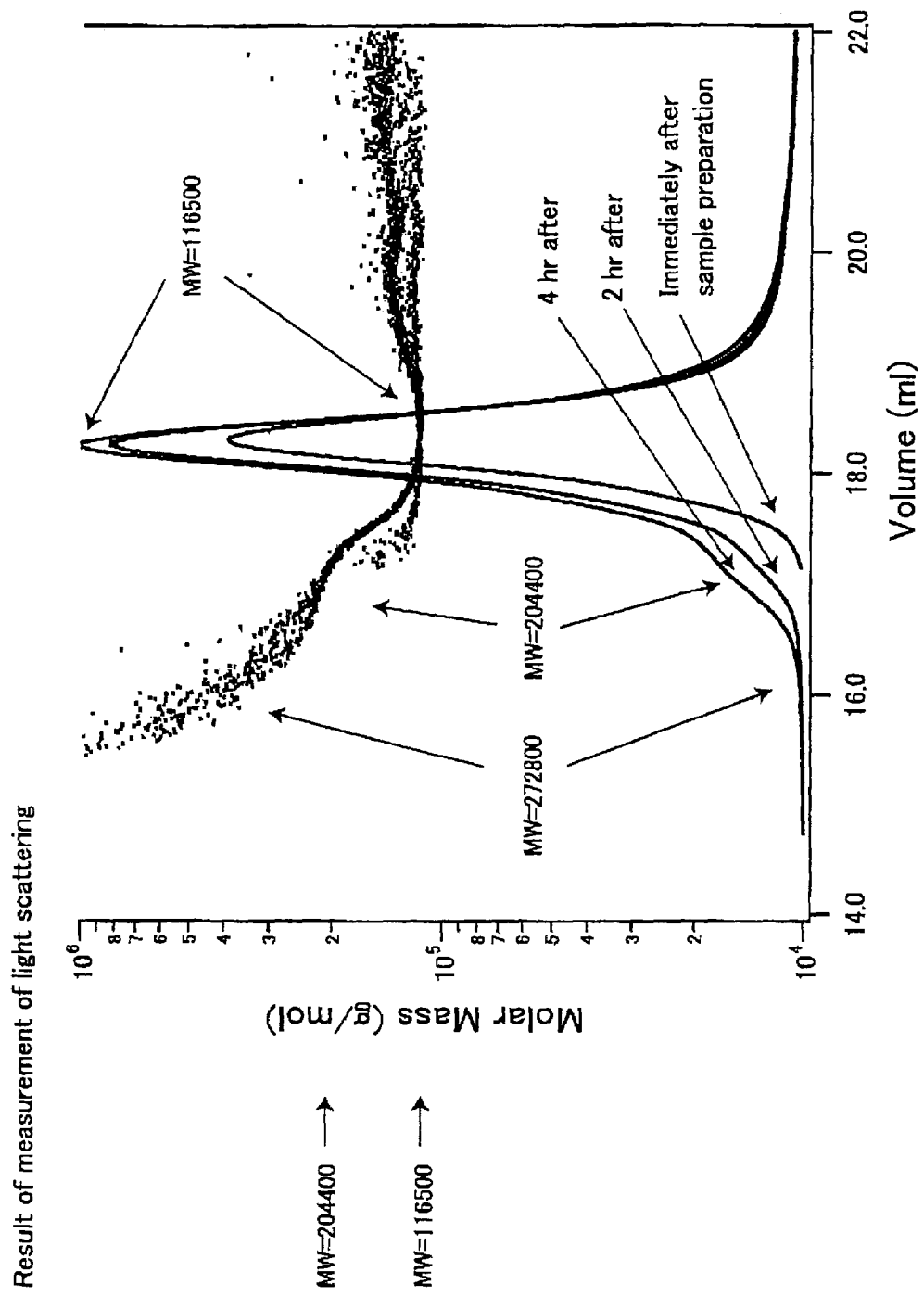
FIG. 3 shows the results of measurement of the formation of multimers by light scattering, using the fluorescent protein derived from coral of the present invention.
Figure 4:
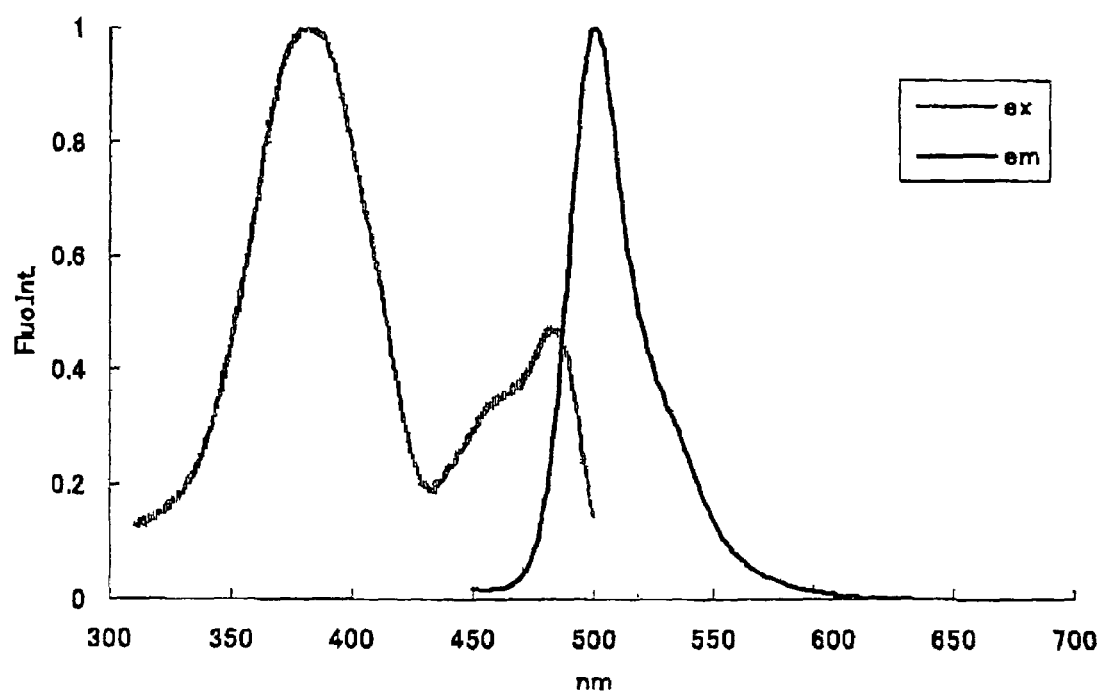
FIG. 4 shows the fluorescence and excitation spectrum (pH 8.0) of a pH-sensitive mutant AG-pH.
Figure 5:
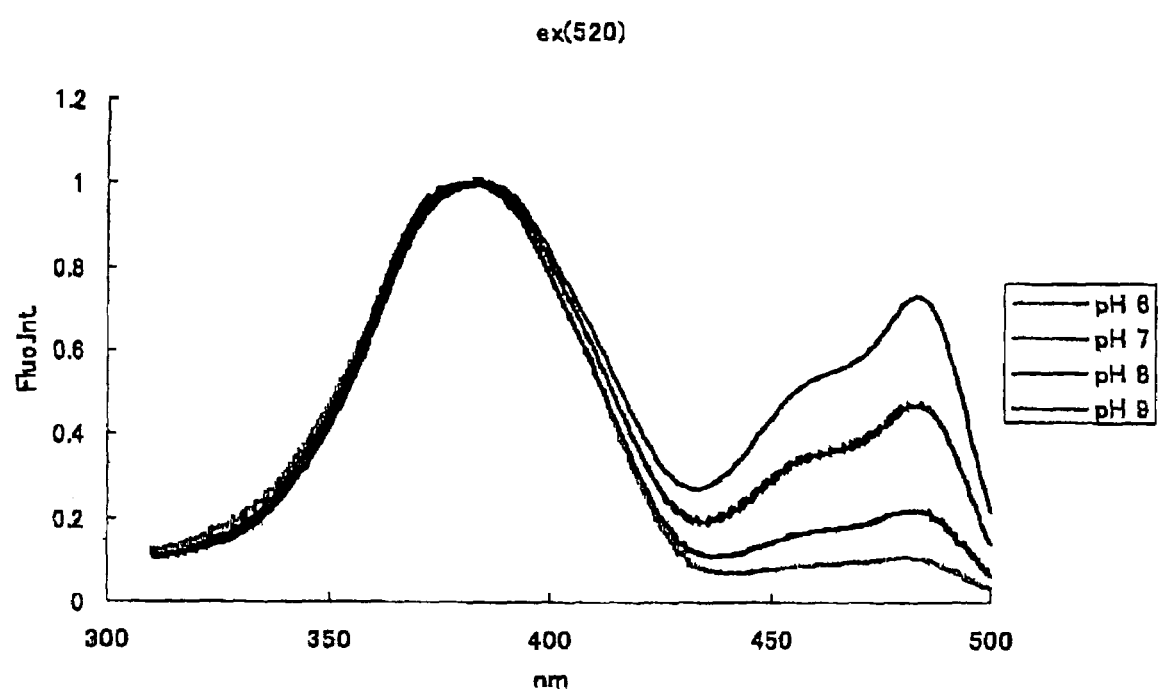
FIG. 5 shows an excitation spectrum at pH 6 to pH 9.
Figure 6:
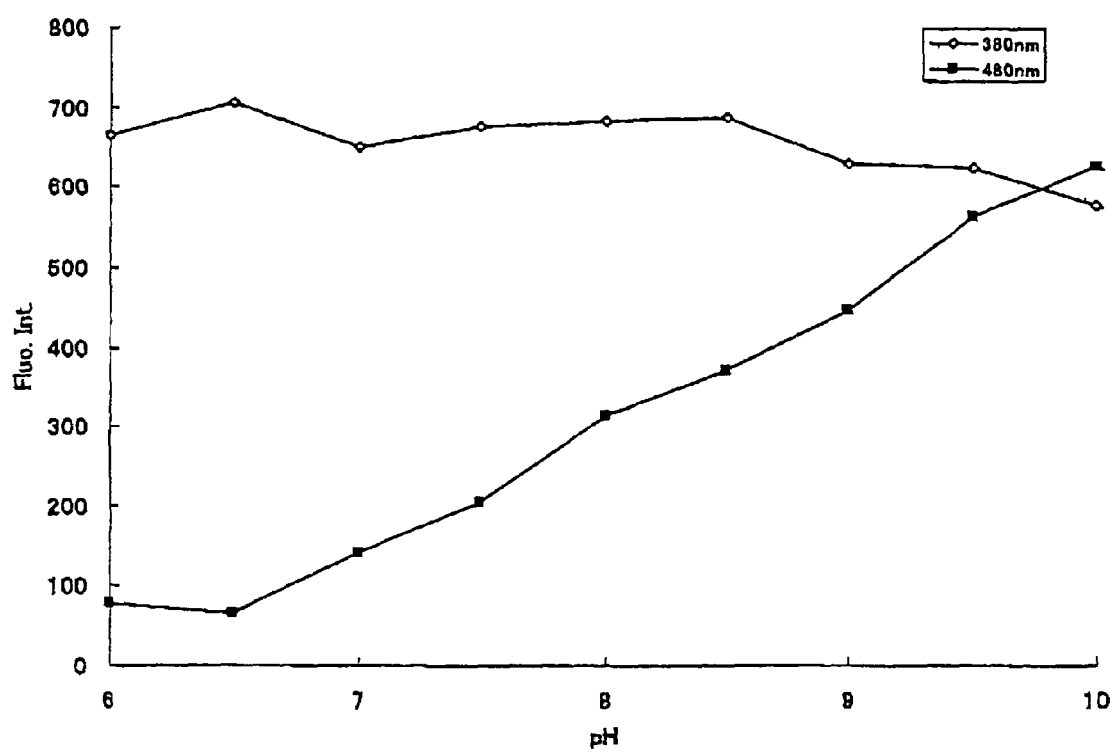
FIG. 6 shows a fluctuation in fluorescence values (520 nm) by pH, when excited at 380 nm and at 480 nm.
Figure 7:
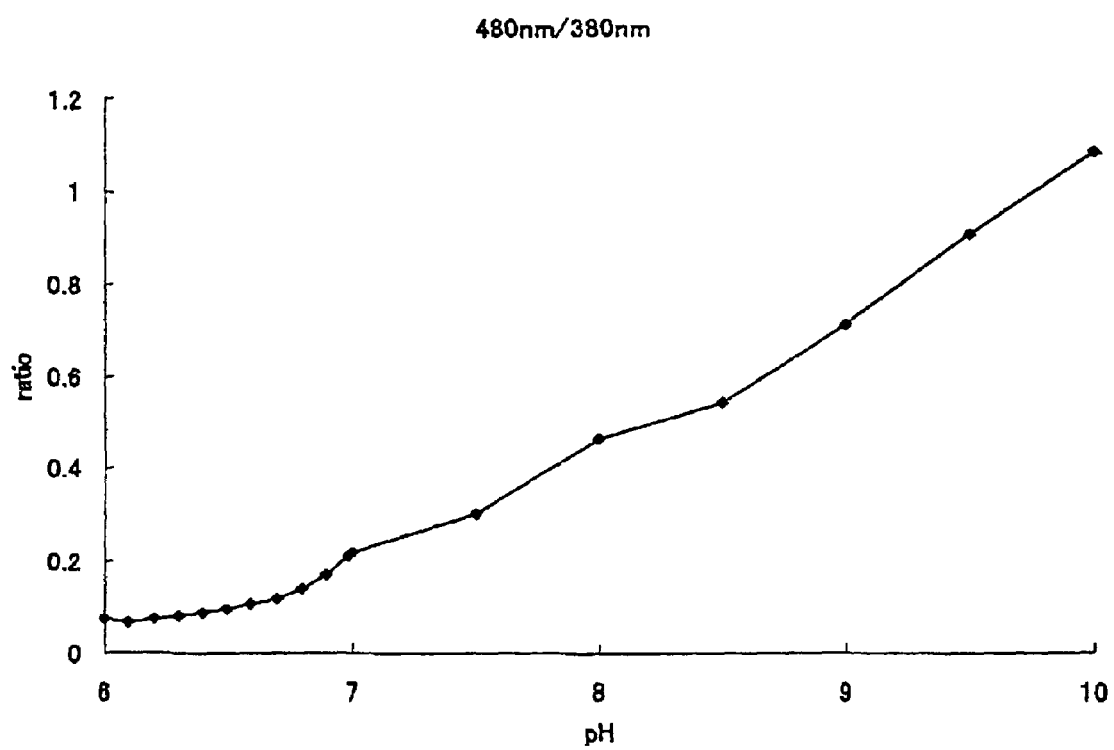
FIG. 7 shows a ratio of fluorescence values (520 nm), when excited at 480 nm and at 380 nm.
Figure 8:
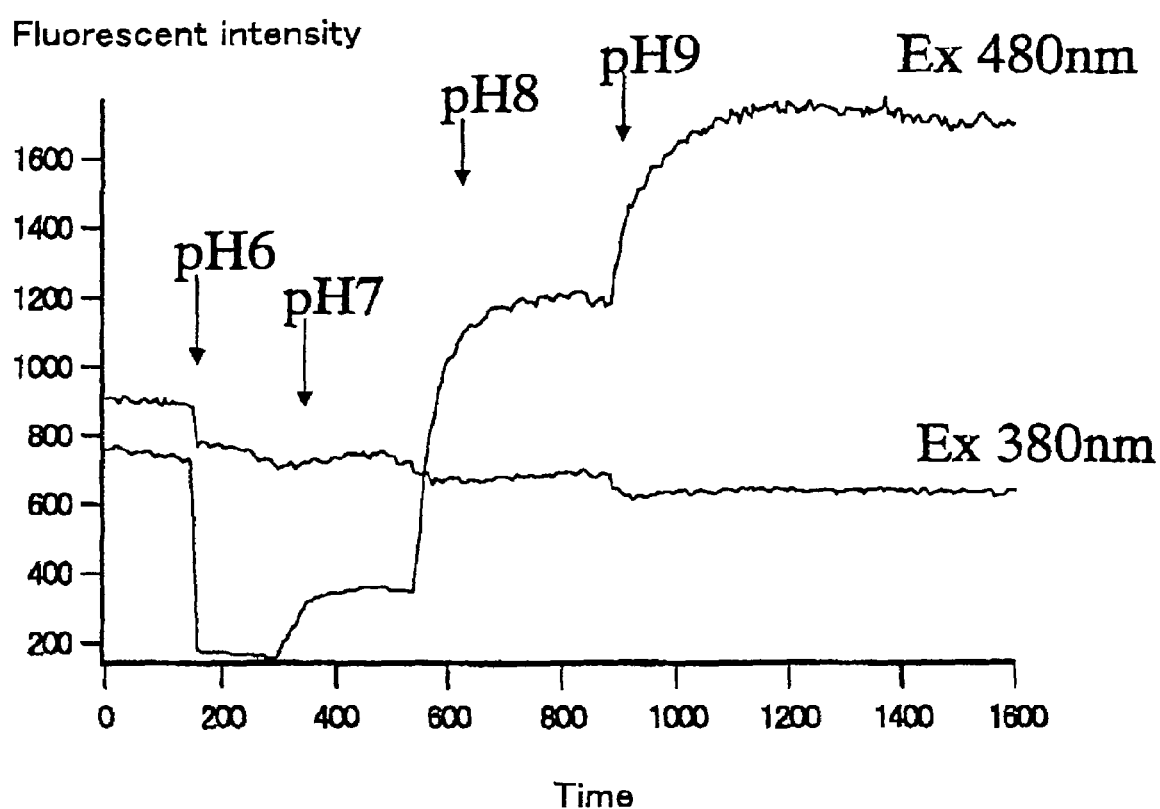
FIG. 8 shows a fluctuation in intracellular fluorescence values by pH, when AG-pH is expressed in HeLa cells and is alternately excited at 380 nm and at 480 nm. 50 hours passed after transfection of HeLa S3; light extinction: 90%; light exposure: 100 ms each; measurement at a time interval of 15 seconds; Ex 380HT15, 480DF10, Em 510 ALP, DM 505DRLP; lens: 40× Uapo/340 NA1.35.
Figure 9:
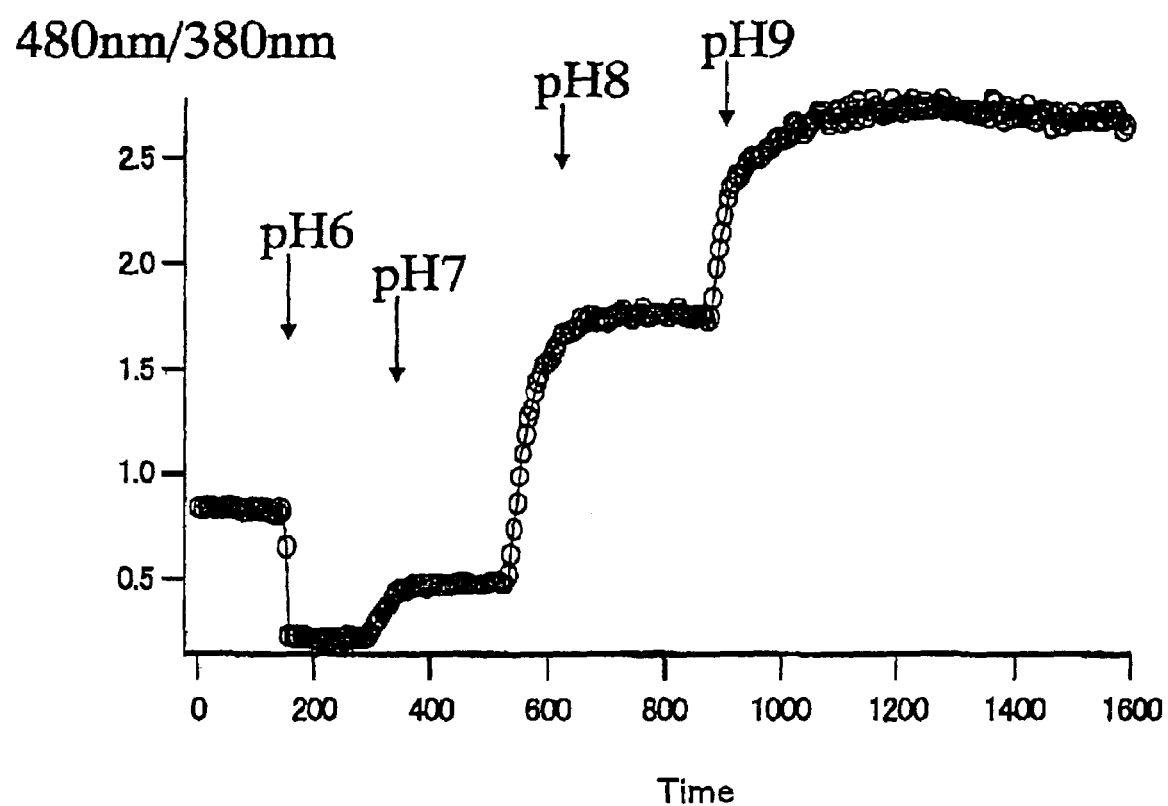
FIG. 9 shows a ratio of intracellular fluorescence values, when AG-pH is expressed in HeLa cells and is alternately excited at 380 ran and at 480 nm.

Measurement results obtained by light scattering are shown in FIG. 3.

Example 2

Production of pH Sensitive Mutant (AG-pH)

Azami-Green has no pH sensitivity and emits a stable green fluorescence at pH 5.5 to pH 12.5. However, when glutamine at position 76 of the Azami-Green is substituted with arginine, asparagine at position 106 with aspartic acid, isoleucine at position 118 with threonine, aspartic acid at position 150 with glycine, and valine at position 157 with aspartic acid, the Azami-Green acquired pH sensitivity. This modified fluorescent protein was named AG-pH.

AG-pH has excitation peaks at 380 nm and at 484 nm. Its fluorescence spectrum shows its peak at 501 nm with any type of excitation. The major excitation peak is at 380 nm, and the Stokes shift is 120 nm, which is an extremely large value. The minor excitation peak at 484 nm increases from pH 6 to pH 10, but the excitation peak at 380 nm does not change. Accordingly, by measuring the ratio of fluorescence values obtained by excitation lights at 380 nm and at 484 nm, it becomes possible to measure pH in vitro or in cells. Among the conventional *Aequorea victoria*-derived GFPs, there is a modified protein (pHluorin), the pH of which can be measured by a fluctuation in two excitation peaks. Differing from the case of AG-pH, however, for this protein, one peak does not take a constant value. Accordingly, the fluorescence in this modified fluorescent protein can be measured by exciting the peak at 380 nm without being influenced by pH (FIGS. 4, 5, 6, 7, 8 and 9).

Example 3

Production of Monomeric Mutant (mAG)

Figure 10:
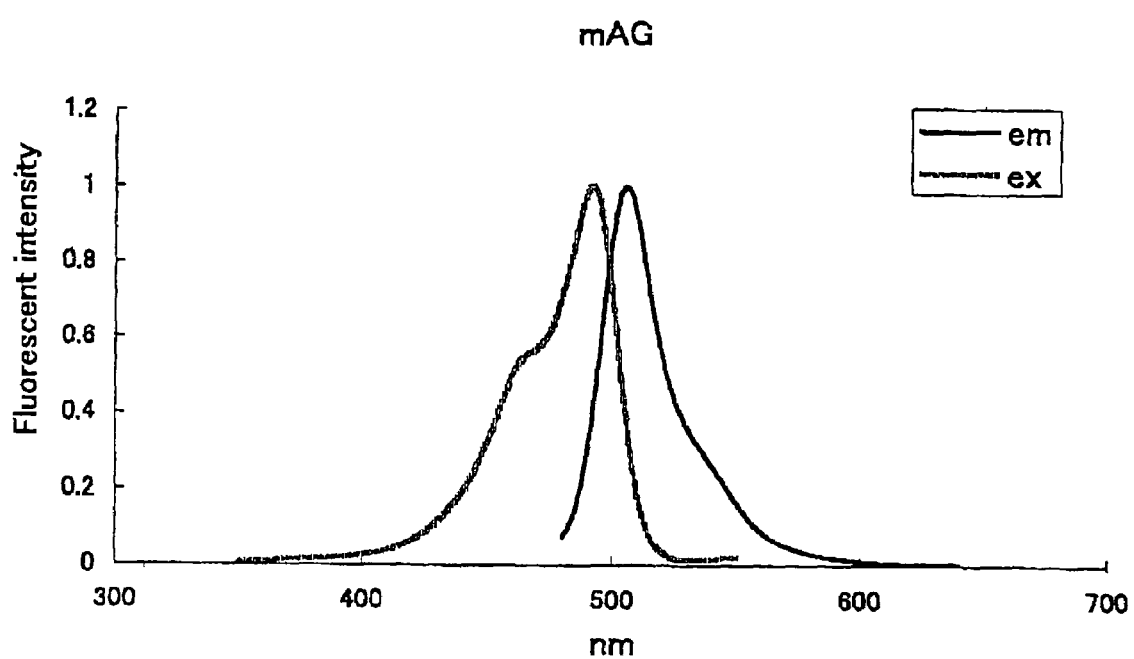
FIG. 10 shows the fluorescence spectrum and excitation spectrum of mAG.
Figure 11:
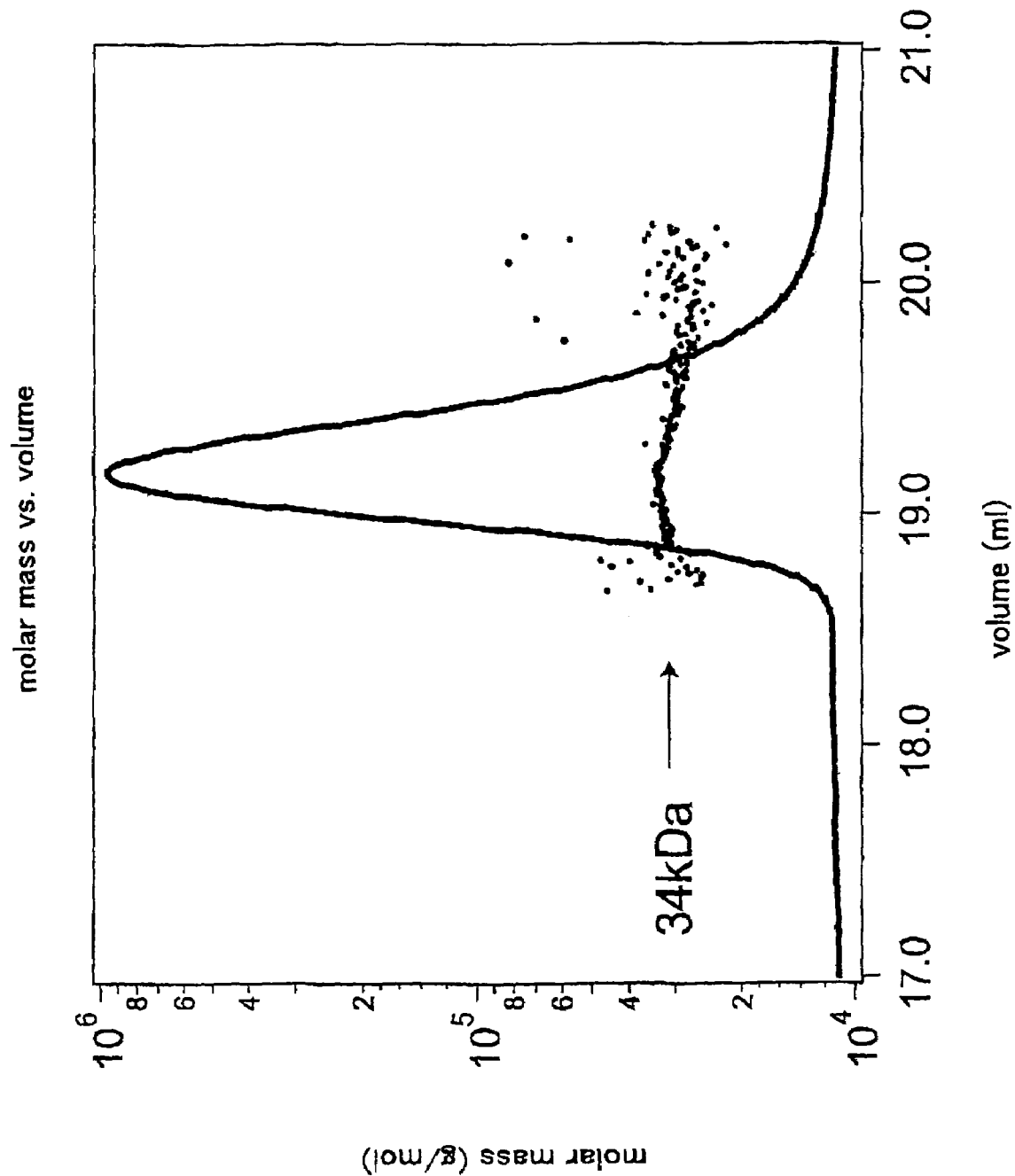
FIG. 11 shows the results of measurement by light scattering.

Azami-Green forms a homotetramer. However, valine at position 123 of the Azami-Green was substituted with threonine, tyrosine at position 188 was substituted with alanine, and phenylalanine at position 190 was substituted with lysine, so as to obtain a mutant that remains as a monomer. The molecular weight of the mutant was confirmed by measurement by light scattering (34 kDa). This modified monomeric fluorescent protein was named mAG. The mAG has a fluorescence maximum wavelength of 505 nm and an excitation maximum wavelength of 492 nm, which are the same values of a wild-type Azami-Green (FIGS. 10 and 11).

INDUSTRIAL APPLICABILITY

The present invention provides a novel fluorescent protein derived from organisms other than a jellyfish. Since the fluorescent protein of the present invention has desired fluorescent properties and has low pH sensitivity, it is useful in the molecular biological analysis.

---

The invention claimed is:

1. An isolated fluorescent protein derived from *Galaxea fascicularis*, which has the following properties:
    (1) the molecular weight is approximately 27,000 D;
    (2) a tetramer is formed in an equilibration state;
    (3) the fluorescence maximum wavelength is 505 nm;
    (4) the molar absorption coefficient is 74,100; and
    (5) the quantum yield is 0.625.

2. The fluorescent protein of claim 1 wherein said fluorescent protein has the following properties:
    (i) the excitation maximum wavelength is 492 nm; and
    (ii) exhibits less fluorescence intensity fluctuation than EGFP through a pH range of 5 to 12.

3. A fusion fluorescent protein consisting of the fluorescent protein of claim 1 and another protein.

4. The fusion protein of claim 3 wherein said another protein is one that localizes in the cell.

5. The fusion protein of claim 4 wherein said another protein is one specific to an intracellular organella.

6. An isolated fluorescent protein having either one of the following amino acid sequences: (a) an amino acid sequence shown in SEQ ID NO: 1; or (b) an amino acid sequence comprising a deletion, substitution and/or addition of one to twenty amino acids with respect to the amino acid sequence shown in SEQ ID NO: 1, and having fluorescent properties.

7. A fluorescent protein having an amino acid sequence wherein Gln at position 76 is substituted with Arg, Asn at position 106 is substituted with Asp, Ile at position 118 is substituted with Thr, Asp at position 150 is substituted with Gly, and Val at position 157 is substituted with Asp, with respect to the amino acid sequence shown in SEQ ID NO: 1.

8. A fluorescent protein wherein Val at position 123 is substituted with Thr, Tyr at position 188 is substituted with Ala, and Phe at position 190 is substituted with Lys, with respect to the amino acid sequence shown in SEQ ID NO: 1.

9. A fluorescent reagent kit which comprises a fluorescent protein
    (i) derived from *Galaxea fascicularis*, which has the following properties:
        (1) the molecular weight is approximately 27,000 D;
        (2) a tetramer is formed in an equilibration state;
        (3) the fluorescence maximum wavelength is 505 nm;
        (4) the molar absorption coefficient is 74,100; and
        (5) the quantum yield is 0.625, or
    (ii) having either one of the following amino acid sequences:
        (a) an amino acid sequence shown in SEQ ID NO: 1; or
        (b) an amino acid sequence comprising a deletion, substitution and/or addition of one to twenty amino acids with respect to the amino acid sequence shown in SEQ ID NO: 1, and having fluorescent properties, or
    (iii) having an amino acid sequence wherein Gln at position 76 is substituted with Arg, Asn at position 106 is substituted with Asp, Ile at position 118 is substituted with Thr, Asp at position 150 is substituted with Gly, and Val at position 157 is substituted with Asp, with respect to the amino acid sequence shown in SEQ ID NO: 1, or
    (iv) having an amino acid sequence wherein Val at position 123 is substituted with Thr Tyr at position 188 is substituted with Ala, and Phe at position 190 is substituted with Lys, with respect to the amino acid sequence shown in SEQ ID NO: 1, or
    (v) a fusion protein consisting of the fluorescent protein (i)-(iv).

10. An isolated DNA which encodes the fluorescent protein of claim 1.

11. A recombinant vector having the DNA of claim 10.

12. An isolated transformant having the DNA of claim 10.

13. An isolated DNA of either one of the following: (a) DNA which encodes the amino acid sequence shown in SEQ ID NO: 1; or (b) DNA which encodes an amino acid sequence comprising a deletion, substitution and/or addition of one to twenty amino acids with respect to the amino acid sequence shown in SEQ ID NO: 1, and having fluorescent properties.

14. An isolated DNA having either one of the following nucleotide sequences: (a) a nucleotide sequence shown in SEQ ID NO: 2; or (b) a nucleotide sequence comprising a deletion, substitution and/or addition of one to sixty nucleotides with respect of the nucleotide sequence shown in SEQ ID NO: 2, and encoding a protein having fluorescent properties.

15. A fluorescent reagent kit which comprises at least one of the following:
    (i) a nucleotide sequence encoding a fluorescent protein derived from *Galaxea fascicularis*, which has the following properties:
        (1) the molecular weight is approximately 27,000 D;
        (2) a tetramer is formed in an equilibration state;
        (3) the fluorescence maximum wavelength is 505 nm;
        (4) the molar absorption coefficient is 74,100; and
        (5) the quantum yield is 0.625; or
    (ii) a nucleotide sequence encoding either one of the following amino acid sequences:
        (a) an amino acid sequence shown in SEQ ID NO: 1; or
        (b) an amino acid sequence comprising a deletion, substitution and/or addition of one to twenty amino acids with respect to the amino acid sequence shown in SEQ ID NO: 1, and having fluorescent properties; or
(iii) a nucleotide sequence encoding an amino acid sequence wherein Gln at position 76 is substituted with Arg, Asn at position 106 is substituted with Asp, Ile at position 118 is substituted with Thr, Asp at position 150 is substituted with Gly, and Val at position 157 is substituted with Asp, with respect to the amino acid sequence shown in SEQ ID NO: 1; or
(iv) a nucleotide sequence encoding an amino acid sequence wherein Val at position 123 is substituted with Thr, Tyr at position 188 is substituted with Ala, and Phe at position 190 is substituted with Lys, with respect to the amino acid sequence shown in SEQ ID NO: 1; or
(v) a nucleotide sequence encoding the amino acid sequence shown in SEQ ID NO: 1; or
(vi) a nucleotide sequence encoding an amino acid sequence comprising a deletion, substitution and/or addition of one to twenty amino acids with respect to the amino acid sequence shown in SEQ ID NO: 1, and encoding a protein having fluorescent properties, a recombinant vector having the DNA, or a transformant having the DNA; or
(vii) a nucleotide sequence shown in SEQ ID NO: 2; or
(viii) a nucleotide sequence comprising a deletion, substitution and/or addition of one to sixty nucleotides with respect of the nucleotide sequence shown in SEQ ID NO: 2, and encoding a protein having fluorescent properties, a recombinant vector having the DNA.

16. A method for analyzing the localization or dynamics of a protein in cells, characterized in that the fusion protein of claim 3 is allowed to be expressed in cells.

* * * * *

UNITED STATES PATENT AND TRADEMARK OFFICE
CERTIFICATE OF CORRECTION

PATENT NO. : 7,247,449 B2 Page 1 of 1
APPLICATION NO. : 10/492081
DATED : July 24, 2007
INVENTOR(S) : A. Miyawaki et al.

It is certified that error appears in the above-identified patent and that said Letters Patent is hereby corrected as shown below:

On the title page, under Foreign Application Priority Data, on the printed patent "October 11, 2001 (JP) 2003-313780" should be --October 11, 2001 (JP) 2001-313780--.

At column 23, line 28 (claim 2, line 5) of the printed patent "5to" should be --5 to--.

At column 24, line 27 (claim 9, line 27) of the printed patent "Thr" should be --Thr,--.

Signed and Sealed this

Seventeenth Day of June, 2008

JON W. DUDAS
*Director of the United States Patent and Trademark Office*